United States Patent [19]

Becker et al.

[11] Patent Number: 4,664,903
[45] Date of Patent: May 12, 1987

[54] REMOVAL OF SULFUR COMPOUNDS FROM GASES

[75] Inventors: Hans Becker, Munich; Michael Heisel, Pullach; Karl Baur, Buchenhain, all of Fed. Rep. of Germany

[73] Assignee: Linde Aktiengesellschaft, Wiesbaden, Fed. Rep. of Germany

[21] Appl. No.: 742,447

[22] Filed: Jun. 7, 1985

[30] Foreign Application Priority Data

Jun. 8, 1984 [DE] Fed. Rep. of Germany ....... 3421508

[51] Int. Cl.⁴ .............................................. C01B 17/02
[52] U.S. Cl. ............................ 423/573 R; 423/245 R; 423/574 L; 423/575; 423/578 R; 585/833
[58] Field of Search ............... 423/575, 574 L, 573 R, 423/245 R, 265, 578 R; 585/833

[56] References Cited

U.S. PATENT DOCUMENTS

| 2,664,345 | 12/1953 | Kohl et al. | 423/575 |
| 2,881,047 | 4/1959 | Townsend | 423/575 |
| 2,987,379 | 6/1961 | Urban | 423/575 |
| 3,103,411 | 9/1963 | Fuchs | 423/575 |
| 3,236,905 | 2/1966 | Otsuka et al. | 208/48 Q |
| 3,676,519 | 7/1972 | Dorn et al. | 208/48 Q |
| 4,088,735 | 5/1978 | Bratzler et al. | 423/245 R |
| 4,155,968 | 5/1979 | Karwat et al. | 423/575 |

OTHER PUBLICATIONS

Hackh's Chemical Dictionary, 4th edition, p. 582.

Primary Examiner—H. T. Carter
Assistant Examiner—Lori S. Freeman
Attorney, Agent, or Firm—Millen & White

[57] ABSTRACT

For the removal of sulfur compounds, especially $H_2S$, from gases that contain hydrocarbons, and/or $CO_2$, the gases are scrubbed with a physical solvent, which is to be regenerated and reused. To obtain sulfur free of hydrocarbons, as well as a practically sulfur-free LPG fraction and optionally a $C_{5+}$ fraction, an oxidizing agent is added to the solvent for reacting the sulfur compounds to elemental sulfur, and the sulfur is separated. The concomitantly absorbed hydrocarbons and/or $CO_2$ can then be desorbed from the separated solvent by physical regeneration and can be recovered.

25 Claims, 2 Drawing Figures

REMOVAL OF SULFUR COMPOUNDS FROM GASES

BACKGROUND OF THE INVENTION

This invention relates to a process for the absorption of sulfur compounds, especially $H_2S$, from hydrocarbon- and/or $CO_2$-containing gases by scrubbing with a physical solvent, and then regenerating and reusing the solvent.

A process step frequently necessary in the processing of raw gas streams is the separation of sulfur compounds, e.g., $H_2S$, COS, $CS_2$, and mercaptans as well as metallic sulfides in some cases. Among these impurities, which generally must be kept away from downstream stages due to their corrosive and catalyst-damaging properties or for other reasons, $H_2S$ is found most frequently in such gas streams, and is generally the predominant impurity.

Examples of gaseous streams that require sulfur compound removal include but are not limited to natural gases, refinery gases, coke oven gases, gases from coal refining, and hydrogen-containing gaseous mixtures. The sulfur compounds are separated from these gaseous streams preferably by a gas scrubbing step with, in particular, a physical solvent (for additional details, see "Erdoel-Kohle-Erdgas-Petrochemic vereinigt mit Brennstoffchemie" (Petroleum-Coal-Natural Gas-Petrochemistry Combined with Fuel Chemistry) vol. 35, issue 8, August 1982 pp. 380–385), incorporated by reference herein. The absorbents employed in that process dissolve the sulfur compounds without chemical reaction and can be desorbed of these sulfur and compounds by expansion and/or stripping.

It has been found, however, that the use of physical scrubbing processes for the desulfurization of gases containing $C_{3+}$ hydrocarbons is normally greatly impeded by coabsorption of these hydrocarbons. The reason for this is that $C_3$ and also $C_4$ hydrocarbons remain at least partially in the $H_2S$ during regeneration of the solvent and the separation of such hydrocarbons from the $H_2S$ is prohibitively expensive. The hydrocarbons in the $H_2S$ not only represent a loss, but they are also technically undesirable in the follow-on Claus plants for the further processing of $H_2S$.

SUMMARY OF THE INVENTION

An object of one aspect of this invention is to provide a process for the desulfurization of gaseous streams, wherein it is possible to recover substantially pure sulfur, essentially free of hydrocarbons, as well as an essentially sulfur-free LPG fraction and optionally a $C_{5+}$ fraction.

In accordance with one aspect of this invention an oxidizing agent is added to the scrubbing agent to react the sulfur compounds to elemental sulfur, the sulfur is separated. According to a further aspect of this invention the concomitantly dissolved hydrocarbons and/or $CO_2$ are separated from the solvent by physical regeneration.

In another aspect of this invention, the sulfur compounds are oxidized in the liquid phase to elemental sulfur and depending on the nature of the sulfur compound, e.g., $H_2S$, to water as well. The resultant sulfur can be removed without difficulties. Thus, in principle, the separation of the sulfur compounds is effected by chemical regeneration. The concomitnatly dissolved hydrocarbons and/or the $CO_2$ do not react with the oxidizing agent and can be conventionally separated from the solvent in a further process step using physical regeneration. Thus, by combining chemical regeneration and conventional physical regeneration, the problem of separating the $H_2S$ from the coabsorbed $C_{3+}$ is economically and technically solved. By $C_{3+}$ fraction is generally meant a fraction consisting predominantly of $C_3$ and $C_4$ but which can comprise also large portion of e.g. $C_2$ and/or $CO_2$ as well as lower concentrations of $C_1$ and $C_{5+}$. Depending on the composition of the feed gas, the composition of the $C_{3+}$ fraction can vary within large ranges.

Suitable solvents for the process of this invention are all conventional physical absorption solutions, especially those selective for sulfur compounds as contrasted with, for example, light hydrocarbons or $CO_2$. These solvents include, in particular, alcohols, such as, e.g., methanol, ketones, N-methylpyrrolidone, dimethylformamide, polyethylene glycol ethers, butyrolactone, aromatic compounds, e.g. toluene and xylene.

Experiments showed that it is especially advantageous to add an oxidizing agent only to the loaded solvent and not before. Otherwise, the sulfur compounds react in the presence of an oxidizing agent so quickly that, when adding the oxidizing agent directly into the scrubbing column or upstream thereof, clogging of the equipment and conduits by the thus-formed sulfur can be avoided only by special measures which increase the cost of the process.

In an advantageous feature of the process of this invention, the sulfur compounds are separated from the solvent in a first process step, and the separation and recovery of the hydrocarbons and/or $CO_2$ take place in a downstream second process step.

Suitably, the oxidizing agent is added in a ratio which is approximately stoichiometric with respect to the reaction of the sulfide compounds. Deviations from stoichiometry lead to incomplete conversion which, though uneconomical, may be desirable for reasons of operating safety. All substances known to oxidize sulfur compounds to sulfur are suitable as the oxidizing agents in the process of this invention. Especially advantageous proved to be oxygen or also ozone-containing oxygen, as well as $SO_x$. In principle, the use of air as the oxidizing agent is likewise possible, but air has an excessive proportion of inert gases which, on the one hand, require expensive separation from the LPG fraction to the obtained and, on the other hand, can exert a stripping effect. This disadvantage is avoided when using oxygen or ozone. Reaction takes place in accordance with $$2H_2S + O_2 \rightarrow 2H_2O + 2/xS_x \qquad (1)$$

The use of $SO_x$, i.e., $SO_2$ and $SO_3$, has the advantage that one product, namely sulfur, can be utilized advantageously. By combustion of part of the thus-produced sulfur, $SO_2$ is produced, scrubbed out with solvent, and added into the $H_2S$-loaded solvent downstream of the raw gas scrubbing column. During this process, the conventional Claus reaction takes place in the liquid phase:

$$2H_2S + SO_2 \rightarrow 2H_2O + 3/xS_x \qquad (2)$$

(x corresponds to the various S-modifications i.e. $S_1$, $S_2$, $S_4$, $S_6$, $S_8$). Both reactions (1) and (2) are strongly exothermic whereby the solvent is heated up during the reaction. It is well known that gas solubility is inversely proportional to temperature whereas the solubility of solids is directly proportional to temperature. As a result, it was recognized that the loaded solvent must be pressure reduced and/or heated in order to expel inert gases from the solvent. Advantageously, the resultant gaseous phases produced during such steps of heating and pressure reduction of the solvent, are recycled into the gas scrubbing step. It was also realized that the sulfur reaction product can be separated from the solvent by lowering the temperature, without expelling the gases remaining in the solvent, namely the concomitantly dissolved hydrocarbons. Because the elemental sulfur is precipitated as a solid phase, the chemical equilibrium is shifted further toward the right, i.e., toward additional sulfur formation. Thus, additional $H_2S$ can react with the oxidizing agent in the solvent to form elemental sulfur.

Consequently, to remove the elemental sulfur, the solvent must be cooled to relatively low temperatures. Addition of the oxidizing agent and/or separation of the thus-produced sulfur can be effected in several stages; also the temperature and/or the pressure of the solvent can be lowered between successive stages. It proved to be especially advantageous to bring the solvent, for separation of the sulfur, to temperatures of between $-50°$ and $+75°$ C., preferably between $0°$ and $+40°$ C., This can take place, for example, in an internally cooled reactor. The sulfur is then separated from the solvent by conventional solid-liquid separation operations, such as, for example, with the aid of a centrifuge or a filter. The respective temperatures depend on the absorbent employed and thus on the temperature at which absorption is carried out.

In many solvents the sulfur is obtained in colloidal form. Therefore, it is preferred to add to the solvent an additive enhancing sedimentation of the thus-formed sulfur and/or accelerating the rate of reaction of this step. The result in this case is that the particle size of the thus-produced sulfur is larger and therefore the sedimentation of the sulfur is eased. Such an additive is, for example, ammonium rhodanite.

Under practical conditions, it is impossible to separate pure elemental sulfur with conventional solid-liquid separating methods. Rather, in all cases a mixture will be separated made up of up to about 50 vol.-% of solvent and 50 vol-% of sulfur. In most cases, the solvent constitutes a relatively valuable chemical which should not be simply discarded. Therefore, in a further development of an aspect of this invention, the solvent, for example, after a fine filtration step, is separated from the residual disposed sulfur by heating the sulfur-solvent mixture. The resultant separated solvent is returned into the solvent cycle. If the solvent at these temperatures is still present in the liquid phase, heating is advantageously conducted to a temperature above the sulfur melting point, especially to about $120°-140°$ C. At these temperatures, two liquid phases evolve, namely elemental sulfur and a supernatant solvent phase. If the solvent is vaporized below the melting temperature of sulfur, it is sufficient to heat the solvent to such a vaporization temperature to separate the solvent from the then solid sulfur.

In still another development of an aspect of this invention, the solvent is freed from the lighter hydrocarbons and/or the $CO_2$, and from the water that may have been formed during the reaction of the sulfur compounds, by heating and/or stripping; and the heavy hydrocarbons that can be removed from the solvent only with difficulty by heating and/or stripping are separated by decanting after adding water or by extraction. Depending on the solvent employed, these hydrocarbons are as low as $C_{5+}$ hydrocarbons or even, for example, as high as $C_{7+}$ hydrocarbons. The heavy hydrocarbons can preferably be removed from the raw gas in a preceding process step. For this purpose, the heavy hydrocarbons are separated from the raw gas preferably by a scrubbing step, wherein the scrubbing step is performed with a partial stream of the loaded solvent from the primary scrubbing stage, and the heavy hydrocarbons are then recovered from the partial stream by decanting after adding water or by extraction. By the addition of water, a separate fraction rich in hydrocarbons splits out and can readily be removed from the solvent. The solvents in the case of water addition are preferably those which can be mixed with water, e.g. methanol or polyethylene glycol ethers. The efficiency of adding water is enhanced if a multistage extraction is used instead of a simple decanting step.

The process of this invention broadens the field of application of physical scrubbing methods, which actually work very economically, to gases with $C_{3+}$ hydrocarbons. By this process, the originally undesirable coabsorption is turned to advantage for separating a practically sulfur-free LPG fraction, e.g., not more than 500 and preferably not more than 5 molar ppm of sulfide in the gas. Moreover, the process opens up a novel use for $SO_2$ obtained, for example, from a flue gas desulfurization.

The process of this invention is applicable to gases containing hydrocarbons and/or $CO_2$ and including sulfur compounds. In this connection, the reaction of the sulfur compounds by oxidation to elemental sulfur is not restricted to $H_2S$; rather, all other sulfur compounds with sulfur of negative valence can be oxidized, such as for example, COS, $CS_2$, mercaptans and for the purposes of this invention such compounds are defined as sulfur compounds.

BRIEF DESCRIPTION OF THE DRAWINGS

This invention will be described in greater detail below with reference to schematically illustrated embodiments wherein.

DETAILED DESCRIPTION OF THE DRAWINGS

Figure 1:
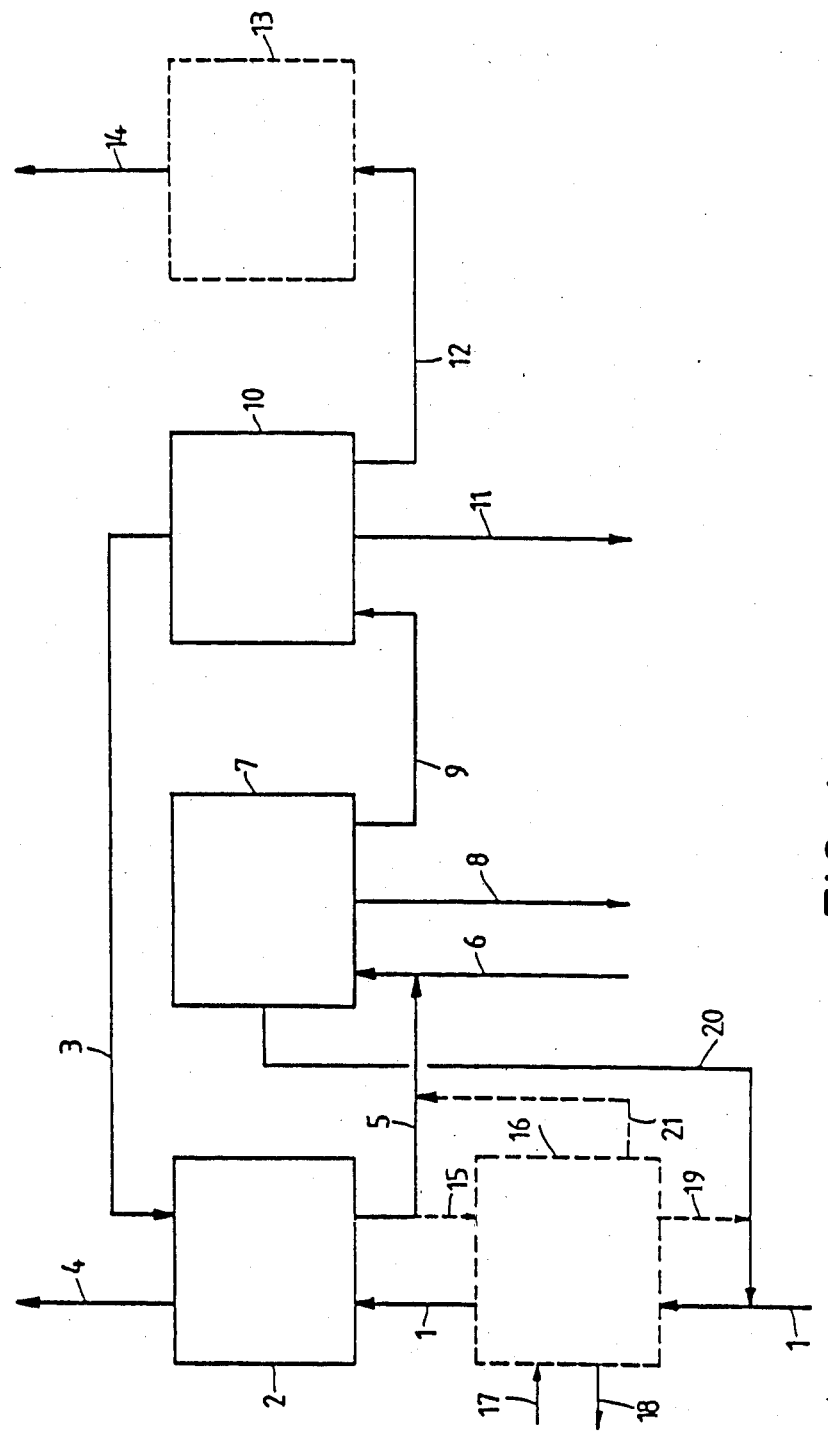
FIG. 1 is a block diagram.

According to the block diagram in FIG. 1, raw gas is introduced via conduit 1 to an absorption stage 2 where the sulfur compounds of the gas are scrubbed out by regenerated solvent introduced via conduit 3. The resultant scrubbed and purified gas is withdrawn via conduit 4.

The solvent loaded with the sulfur compounds is discharged via conduit 5 and combined with $SO_2$ from conduit 6, for example. The resultant mixture is introduced into a holding tank 7 wherein reaction to sulfur takes place in accordance with the Claus reaction, and the elemental sulfur is withdrawn via conduit 8. The desulfurized solvent in conduit 9 is then passed to regeneration stage 10 wherein the solvent is regenerated by heating and/or stripping, and in this way the $C_4$ and lighter hydrocarbons as well as water are separated. The regenerated solvent is recycled via conduit 3, water is removed via conduit 11, and the LPG (liquefied petroleum gas) fraction conducted via conduit 12 is optionally subjected to fine purification 13 and obtained as the product via 14. Another option illustrated in the dashed-line block diagram is the possibility of separating heavy hydrocarbons ($C_{5+}$ hydrocarbons). For this purpose, a partial stream of the loaded solvent is passed via conduit 15 to a separating stage 16, wherein it contacts not only entering raw gas but also water introduced via conduit 17, thus forming a hydrocarbon-enriched phase. This phase can be withdrawn via conduit 18, for example, by decanting. Any gases liberated during this step can be reintroduced into the raw gas stream by way of conduit 19. The same holds true for gaseous phases released during chemical regeneration, especially by raising the temperature or lowering the pressure. These gaseous phases can likewise be added to the raw gas stream via conduit 20. The raw gas, optionally freed of the heavy hydrocarbons, is then introduced into the absorption stage 2 and, as the occasion admits, the partial stream of solvent freed of heavy hydrocarbons, is added to the solvent cycle via conduit 21.

Figure 2:
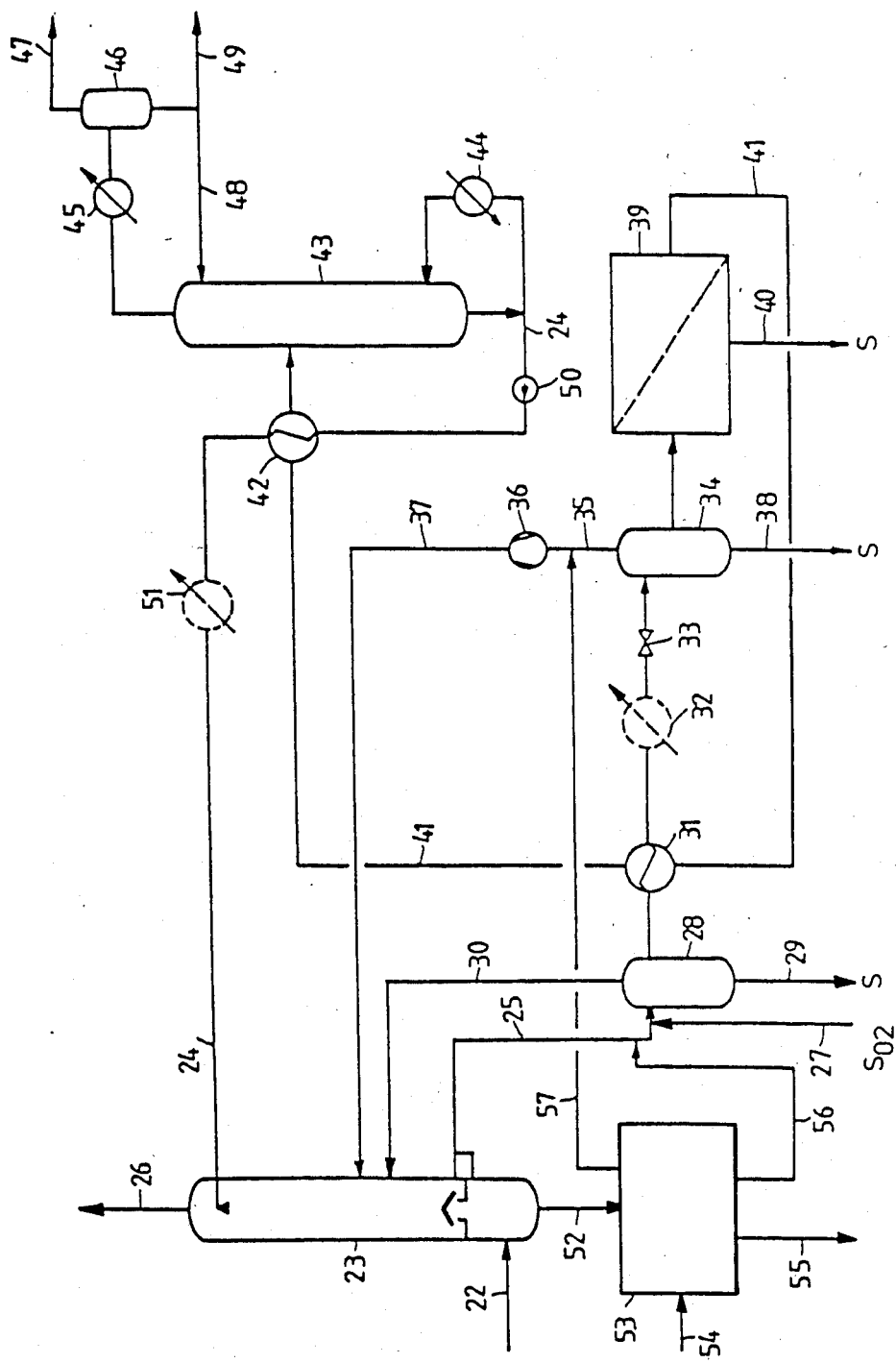
FIG. 2 is a flow chart of a preferred embodiment of the invention.

Accordingly to FIG. 2, $H_2S$-containing raw gas is introduced in an amount of 10,000 kmol/h via conduit 22 to the bottom of a scrubbing column 23 under a pressure of 80 bar and at a temperature of 40° C., whereas regenerated solvent is fed to the upper section of the scrubbing column by way of conduit 24. The raw gas has the following composition:

| | | |
|---|---|---|
| $CH_4$ | 81.8 | mol % |
| $C_2$ | 8.4 | mol % |
| $C_3$ | 3.1 | mol % |
| $C_4$ | 1.1 | mol % |
| $C_5$ | 0.5 | mol % |
| $C_6$ | 0.1 | mol % |
| $C_7$ | 0.1 | mol % |
| $C_8$ | 0.02 | mol % |
| $C_9$ | 0.01 | mol % |
| $N_2$ | 0.6 | mol % |
| $H_2S$ | 4.0 | mol % |
| $H_2O$ | saturated | |

The solvent is polyethylene glycol ether.

The $H_2S$ and higher hydrocarbons ($C_{3+}$) are absorbed by the solvent from the latter and exit from the column via conduit 25. Purified gas, 8,872 kmol/h, is withdrawn overhead via conduit 26 at a temperature of 42° C. (80 bar). The purified gas has the following composition:

| | | |
|---|---|---|
| $CH_4$ | 89.80 | mol % |
| $C_2$ | 8.77 | mol % |
| $C_3$ | 0.63 | mol % |
| $C_4$ | 0.69 | mol % |
| $C_5$ | 0.01 | mol % |
| $C_6$-$C_9$ | traces | |
| $N_2$ | 0.68 | mol % |
| $H_2S$ | 230 | ppm |
| $SO_2$ | 1 | ppm |

Via conduit 27, the loaded solvent is admixed, for example, with $SO_2$ in dissolved, gaseous or liquid form, and the mixture is fed into a holding tank 28 for reacting the $H_2S$ into water and elemental sulfur. A portion of the elemental sulfur can be withdrawn via conduit 29. Inert gases released by virtue of the increased temperature resulting from the reaction can be returned via conduit 30 into the scrubbing column 23. After being cooled in a heat exchanger 31 against sulfur-free solvent (as well as after optional further cooling in a cooler 32) and being expanded via valve 33, the loaded solvent is introduced into an inert gas separator 34. The inert gases, especially $N_2$, as well as methane and $C_2$ hydrocarbons, are liberated during expansion to about 5 bar. They are then withdrawn overhead via conduit 35, compressed to the pressure of the scrubbing column of 80 bar, in 36, and recycled via conduit 37 into the upper zone of the scrubbing column. Any sulfur that has crystallized owing to the expansion and accompanying cooling can be discharged by way of conduit 38.

The solvent is then introduced into a fine separating stage for sulfur, denoted by 39, from which the sulfur is discharged by way of conduit 40. The sulfur fine separating stage consists of a conventional solid-liquid separation device like e.g. a filter or a centrifuge and e.g. a thermal treatment of the thus separated sulfur which contains still up to 50% of solvent. By the thermal treatment, the sulfur is molten and two liquid phases form, the one being the solvent the other the molten sulfur. The two phases are separated and the solvent is, after cooling, recycled to the inlet end of the fine separation.

The separation step yields 74.6 kmol/h of $S_8$ under normal pressure and at a temperature of 120° C. This sulfur contains, besides less than 20 ppm of hydrocarbons and $N_2$, less than 10 ppm of $H_2S$, and water (1,000 ppm).

The sulfur-free solvent is then discharged via conduit 41, heated in heat exchanger 31 and in a heat exchanger 42 against regenerated solvent, and introduced into a regenerating column 43. In the regenerating column, concomitantly dissolved hydrocarbons as well as water are driven out of the solvent by means of reboiler 44. After cooling in 45 and separation of condensate in 46, an LPG fraction is withdrawn via conduit 47 with a temperature of 50° C. under a pressure of 4 bar. This LPG fraction (640 kmol/h) has the following composition:

| | | |
|---|---|---|
| $CH_4$ | 33.28 | mol % |
| $C_2$ | 9.69 | mol % |
| $C_3$ | 39.69 | mol % |
| $C_4$ | 15.94 | mol % |
| $C_5$ | 0.94 | mol % |
| $C_6$ | 0.31 | mol % |
| $C_7$ | 0.15 | mol % |
| $H_2S$ | 30 | ppm |
| $H_2O$ | saturated | |

Water is removed from the separator 46 and passed on, in part, via conduit 48 to the head of regenerating column 43 as reflux for solvent regeneration and, the remainder of the water is discharged via conduit 49.

Regenerated solvent is withdrawn from the sump of regenerating column 43 via conduit 24, passed through a pump 50, cooled in heat exchanger 42 and optionally against external refrigeration in a cooler 51 and introduced into the scrubbing column 23.

If it is desired to obtain the $C_{5+}$ hydrocarbons separately, the following system can be used: A partial stream of the solvent is withdrawn via conduit 52 from the lower section of scrubbing column 23 below the "chimney tray", and passed onto a $C_{5+}$ separation 53. Water is added via conduit 54 so that a phase rich in hydrocabons is produced which is withdrawn via conduit 55. This $C_{5+}$ fraction (63 kmol/h) has a pressure of e.g. 5 bar, a temperature of e.g. 35° C., and the following composition:

| | |
|---|---|
| $C_5$ | 68.25 mol % |
| $C_6$ | 12.70 mol % |
| $C_7$ | 14.28 mol % |
| $C_8$ | 3.17 mol % |
| $C_9$ | 1.60 mol % |
| $H_2S$ | 20 ppm |
| $H_2O$ | saturated |

Aqueous solvent can then be introduced via conduit 56 into the solvent cycle, particularly into conduit 25. Any gases released during decantation can be returned by way of conduit 57.

The preceding embodiments can be repeated with similar success by substituting the generically or specifically described reactants and/or operating conditions of this invention for those used in the preceding embodiments.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. In a process for the removal of sulfur compounds from gases that include a $C_{3+}$ hydrocarbon fraction, comprising scrubbing the gas with a physical solvent which absorbs the sulfur compounds and gases that include a $C_{3+}$ fraction in the scrubbing stage and regenerating and reusing the physical solvent, the improvement comprising withdrawing the loaded solvent from the scrubbing stage; adding an oxidizing agent to the physical solvent to react the sulfur compounds to elemental sulfur; separating the resultant sulfur from the solvent; and further separating and recovering the co-absorbed gases that include a $C_{3+}$ fraction from the solvent by physical regeneration.

2. A process according to claim 1, wherein the oxidizing agent is added to the solvent after the sulfur compounds are absorbed therein.

3. A process according to claim 1, comprising conducting, in a first process step, the separation of the sulfur compounds from the solvent and, in a subsequent, second process step, conducting the separating and recovery of the gases including a $C_{3+}$ fraction.

4. A process according to claim 1, wherein several different oxidizing agents are added in separate oxidizing stages.

5. A process according to claim 1, said oxidizing agent being added in an approximately stoichiometric proportion with respect to the reaction of the sulfur compounds.

6. A process according to claim 1, wherein the oxidizing agent is oxygen.

7. A process according to claim 1, wherein the oxidizing agent is $SO_2$ and/or $SO_3$.

8. A process according to claim 1, wherein the addition of the oxidizing agent and/or the separation of sulfur from the solvent is performed in several series-arranged stages; and that, between individual stages, the temperature and/or the pressure of the solvent is lowered.

9. A process according to claim 1, wherein the solvent loaded with sulfur compounds is brought to a higher pressure and/or is heated.

10. A process according to claim 9, wherein gaseous phases forming during raising of the temperature and/or lowering of the pressure of the solvent are recycled into the scrubbing step.

11. A process according to claim 1, wherein the solvent, to separate the sulfur, is brought to temperatures of between $-50°$ and $+75°$ C.

12. A process according to claim 1, wherein the solvent, to separate the sulfur, is brought to temperatures of between $0°$ and $+40°$ C.

13. A process according to claim 1, further comprising adding to the solvent an additive that accelerates the reaction rate of the reaction and/or enhances the sedimentation of the thus-formed sulfur.

14. A process according to claim 1, wherein the separated sulfur has solvent in admixture therewith, and the solvent withdrawn together with the sulfur is separated by heating the sulfur-solvent mixture, the resultant solvent being returned into the solvent cycle.

15. A process according to claim 14, wherein the sulfur-solvent mixture is heated to between $120°$ and $140°$ C., and the sulfur is separated in the liquid form from the solvent.

16. A process according to claim 1, wherein the solvent is separated, by heating and/or stripping, from lighter hydrocarbons and/or the $CO_2$ and from any water produced during the reaction of the sulfur compounds.

17. A process according to claim 1, wherein $C_{5+}$ hydrocarbons are separated from the solvent by decanting after addition of water and/or by extraction.

18. A process according to claim 16, wherein heavy hydrocarbons are removed from the raw gas in a process step preceding the reaction of the sulfur compounds.

19. A process according to claim 18, said heavy hydrocarbons being separated from the raw gas by means of a scrubbing step wherein the scrubbing step is performed with a partial stream of the loaded solvent from the sulfur scrubbing stage; and the heavy hydrocarbons are separated from said partial stream by decanting after addition of water and/or by extraction.

20. A process according to claim 1, further fractionating the gases including a $C_{3+}$ fraction to form an essentially sulfur-free LPG fraction.

21. A process according to claim 1, further fractionating the gases including a $C_{3+}$ fraction to form a $C_{5+}$ fraction.

22. A process according to claim 20, wherein the sulfur-free LPG fraction has less than about 5-500 molar ppm of sulfide.

23. A process according to claim 1, wherein the solvent is an alcohol, a ketone, a polyethylene glycol ethers or an aromatic hydrocarbon.

24. A process according to claim 1, wherein the solvent is methanol, N-methylpyrrolidone, dimethylformamide, polyethylene glycol ether, butyrolactone, toluene or xylene.

25. A process according to claim 13, wherein the additive is ammonium rhodanide.

* * * * *